(12) United States Patent
Gidekel

(10) Patent No.: US 9,491,950 B2
(45) Date of Patent: Nov. 15, 2016

(54) TERMITE AND OTHER WOOD DAMAGING INSECT CONTROL

(71) Applicant: Manuel Gidekel, Santiago (CL)

(72) Inventor: Manuel Gidekel, Santiago (CL)

(73) Assignee: ICY T, Santiago (CL)

( * ) Notice: Subject to any disclaimer, the term of this patent is extended or adjusted under 35 U.S.C. 154(b) by 0 days.

(21) Appl. No.: 14/120,777

(22) Filed: Jun. 26, 2014

(65) Prior Publication Data

US 2016/0174568 A1   Jun. 23, 2016

Related U.S. Application Data

(60) Provisional application No. 61/957,617, filed on Jul. 8, 2013.

(51) Int. Cl.
*A01N 65/00* (2009.01)
*A01N 63/02* (2006.01)
*B27K 3/00* (2006.01)

(52) U.S. Cl.
CPC ............... *A01N 63/02* (2013.01); *B27K 3/002* (2013.01)

(58) Field of Classification Search
CPC ...................................................... A61K 36/00
USPC ........................................................ 424/725
See application file for complete search history.

(56) References Cited

U.S. PATENT DOCUMENTS

2014/0283443 A1*  9/2014  Werner ................. A01C 11/00
                                                                    47/17

* cited by examiner

*Primary Examiner* — Michael Meller
(74) *Attorney, Agent, or Firm* — John Dodds

(57) ABSTRACT

The present invention provides for the first time a biological system which provides the dual function of killing termites and other wood damaging insects while also producing a by-product substance having the capability of repairing damage by termites and other insects to wood and related cellulosic products.

The present invention, a biological system, toxic to termites, is provided which produces a means by which damage caused by termites is repaired, said means comprising a by-product produced by a modification of the bacteria of the genus *Gluconacetobacter*. Preferably, the biological system is in the form of toxic bait.

1 Claim, 6 Drawing Sheets

>Gluconacetobacter malus
GTGTAGTTAAGTTTTTACAATACAAGTCGCACGATCTTTTCGGGTTTAGTGGCGGACGGGT
GAGTAACGCGTAGGGATTTATCCACGGGTGGGGAATAATTTTGGAAAACTGAAGCTAATCC
CGCATGACACCTGAGGGTCAAAGGCGCAAGTCCCCTGTGGAGAAACCTGCTTTCAATTACC
TAGTTGGGGGGGTAAAGGCCTACCAAGGCAATGATCAATAGCTGGTCTGAGAGGATGATCA
CCCACACTGGGACTGAAACACGGCCCAAACTCCTACGGGAGGCAGCAGTGGGAAATATTGA
ACAATGGGCGCAACCCTGATCCACCAATGCCGCGTGTGTGAAAAAGGTTTTCGGATTGTAA
AGCATTTTCAGCGGGGACAATGATGACGGTCCCCGCAAAAAAACCCCCGGCTAATTTCGTG
CCAGCACCCGCGGTAATACAAAGGGGGCAAGCGTTGCTCGAAATGACTGGGCGTAAAGGGC
GCGTAGGCGGTTGACACAGTCAAATGTAAAATTCCCGGGTTTAACCTGGGGGCTGCTTTTG
ATACGTGGCAACTAAAGTGTGAAAAAGGGGTTGTGAAATTCCCAGTGTAGAGGTGAAATTCG
TAAATATTGGAAAAAACACCGGGGGCAAAGGCGGCAACCTGGCTCATGACTGACCCTGAGG
CGCAAAAGCGTGGGGAGCAAACAGGATTAAATACCCTGGTAGTCCACGCTGTAAACAATGT
GTGCTGAATGTTGGGTGACTTTGTCATTCAGTGTCGTATTTAACGCGATAAGCACACCGCC
TGGGGAGTACGGCCGCAAGGTTAAAACTCAAAGAAATTGACGGGGCCCGCACAAGCGGGG
GAGCATGTGGTTTATTTCAAAGCAACGCGCAAAACCTTACCAGGGCTTGACATTGGGAAGG
CCGTGTCCAGAAATGGGCATTTTCTCGCAAAAAAACCTCAACCAACAGGTGCCTGCATGGT
TTGTCTCCCTCTCCGGTCCGGGAA

SEQUENCE LISTING

<160> NUMBER OF SEQ ID NOS: 1

<210> SEQ ID NO 1
<211> LENGTH: 1000
<212> TYPE: DNA
<213> ORGANISM: Komagataeibacter xylinus

<400> SEQUENCE: 1
gtgtagttaa gttttacaa tacaagtcgc acgatctttt cgggtttagt ggcggacggg        60

-continued

```
tgagtaacgc gtagggattt atccacgggt ggggaataat tttggaaaac tgaagctaat      120
cccgcatgac acctgagggt caaaggcgca agtcccctgt ggagaaacct gctttcaatt      180
acctagttgg gggggtaaag gcctaccaag gcaatgatca atagctggtc tgagaggatg      240
atcacccaca ctgggactga aacacggccc aaactcctac gggaggcagc agtgggaaat      300
attgaacaat gggcgcaacc ctgatccacc aatgccgcgt gtgtgaaaaa ggttttcgga      360
ttgtaaagca ttttcagcgg ggacaatgat gacggtcccc gcaaaaaaac ccccggctaa      420
tttcgtgcca gcacccgcgg taatacaaag ggggcaagcg ttgctcgaaa tgactgggcg      480
taaagggcgc gtaggcggtt gacacagtca aatgtaaaat tcccgggttt aacctggggg      540
ctgcttttga tacgtggcaa ctaaagtgtg aaaaagggtt gtgaaattcc cagtgtagag      600
gtgaaattcg taaatattgg aaaaaacacc ggggggcaaag gcggcaacct ggctcatgac      660
tgaccctgag gcgcaaaagc gtggggagca aacaggatta aatacccctgg tagtccacgc     720
tgtaaacaat gtgtgctgaa tgttgggtga ctttgtcatt cagtgtcgta tttaacgcga      780
taagcacacc gcctggggag tacggccgca aggttaaaac tcaaagaaat tgacggggc      840
ccgcacaagc gggggagcat gtggtttatt tcaaagcaac gcgcaaaacc ttaccagggc      900
ttgacattgg gaaggccgtg tccagaaatg gcattttct cgcaaaaaaa cctcaaccaa      960
caggtgcctg catggtttgt ctccctctcc ggtccgggaa                          1000
```

TERMITE AND OTHER WOOD DAMAGING INSECT CONTROL

This application claims benefit of 61/957,617 filed on Aug. 8, 2013

SEQUENCE LISTING

The instant application contains a Sequence Listing which has been submitted electronically in ASCII format and is hereby incorporated by reference in its entirety. Said ASCII copy, created on Feb. 25, 2016, is named Termites_SL.txt and is 1,672 bytes in size.

FIELD OF THE INVENTION

The present invention embraces a biological system that can be used as bio-repair, insecticide, termiticide and bio-additive. This invention provides a biomaterial based in a bacteria that produces cellulose from sugar derivate. The biological system increases the resistance and flexural strength and also has an insecticide effect.

BACKGROUND OF THE INVENTION

Soil termites, also known as subterranean termites, are the most destructive termites in the United States. These insects, and other related insects can cause a lot of damage and should be controlled upon discovery.

Hundreds of thousands of termites in a colony well-organized among workers, soldiers and Queens tunnel 24 hours a day through soil and into the wooden frames of houses, fences and buildings providing new sources of cellulose for the entire colony.

If left untreated, termites can destroy the entire value of a home. According to the National Pest Management Association, termites are costing Americans more than $5 billion in damage each year. This is more than fire and floods combined. Destruction is boundless, because any home, regardless of design, can offer the ideal combination of heat, moisture and food for termites. In addition, many plans for housing are not covered by insurance for such damages. Without insurance protection, serious problems in selling a house may arise. Many lenders require a termite bond before lending money to homebuyers.

SUMMARY OF THE INVENTION

The present invention provides for the first time a biological system which provides the dual function of killing termites and other wood damaging insects while also producing a by-product substance having the capability of repairing damage by termites and other insects to wood and related cellulosic products.

In a particular embodiment of the present invention, a biological system, toxic to termites, is provided which produces a means by which damage caused by termites is repaired, said means comprising a by-product produced by a modification of the bacteria of the genus *Gluconacetobacter*. Preferably, the biological system is in the form of toxic bait.

In another embodiment of the present invention, a process is provided for killing termites and other wood damaging insects and for repairing damage to wood and related cellulosic products caused by termites comprising the steps of:

(a) Providing a modification of the bacteria of the genus *gluconacetobacter* toxic to termites and wood damaging insects, and insects family like acaridae and nematodes
(b) Converting said bacterial modification into a bait attractive to termites and other insects as a source of food;
(c) Allowing said bacterial modification to produce by-product ooze capable of repairing would damage by termites and other wood damaging insects.

The by-product ooze is toxic to termites and other insects and non-toxic to humans.

BRIEF DESCRIPTION OF THE DRAWINGS

FIG. 1. shows the 16S ribosomal RNA gene sequence of *Gluconacetobacter malus*.

DETAILED DESCRIPTION OF THE INVENTION

Figure 2:
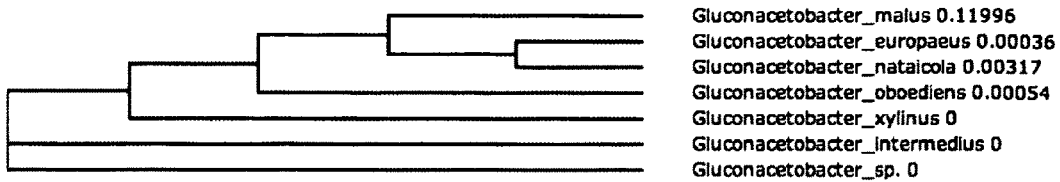
FIG. 2. illustrates the phylogenetic tree of 16S ribosomal RNA gene sequence of *Gluconacetobacter malus* with other species with high similarity.

A *Gluconacetobacter* bacterium from an apple was isolated. First, the apple was washed with distilled water and then it was crashed in 25 mL of sterile distilled water as well. The extract produced was incubated for 10 days at room temperature for the bacteria production. After this incubation, serial dilutions of the culture were done on LB agar plates and were incubated at 27-Celsius degrees for 2 days. The most diluted colonies corresponding to the white colored colonies were selected and analyzed by 16srRNA-PCR procedure using F8 forward primer (AGAGTTT-GATCCTGGCTCAG) and R1492 reverse primer (GGT-TACCTTGTTACGACTT) (Weisburg et al., 1991; Baker et al., 2003). The sequence obtained (FIG. 1) was analyzed by BLAST and had 92% of identity with *Gluconacetobacter intermedius* (gi: 594191428), *Gluconacetobacter xylinus* (gi: 359803333), *Gluconacetobacter* sp. (gi: 323482039), *Gluconacetobacter oboediens* (gi: 359803727), *Gluconacetobacter europaeus* (gi: 380292627) and *Gluconacetobacter nataicola* (gi: 343200325). So, we called our bacteria strains as *Gluconacetobacter malus*. Also, a phylogenetic tree analysis using ClustalW2-Phylogeny program was performed (FIG. 2).

An evaluation of cellulose yield was done. *G. malus* was cultured in liquid mediums using different nutrient sources (glucose and sugar derivate) for 2 weeks at 27 Celsius-degrees without shaking (static culture) to produce cellulose. A cellulose yield of 128.8 g/L, 119 g/L, 111.9 g/L, 99.8 g/L and 94.9 g/L was produced by G. malus. From glucose, sugar beet derivates 1, 2, 3 and 4, respectively (shown in Table 1).

TABLE 1

Cellulose yield using different nutrient sources.

| Sugar Source | Cellulose Yield (gr cellulose/ml culture) | Cellulose Yield (gr cellulose/L culture) |
|---|---|---|
| Glucose | 0.13 | 128.8 |
| Sugar derivatives 1 | 0.12 | 119 |
| Sugar derivatives 2 | 0.11 | 111.9 |
| Sugar derivatives 3 | 0.10 | 99.8 |
| Sugar derivatives 4 | 0.09 | 94.9 |

Example 1

Biological System as Bio-Repair

To test the biological system as bio-repair, physical properties of these celluloses were assayed by doing a Dynamic Mechanic Analysis (DMA). Resistance and mechanical strength of cellulose are five times more in comparison with wood-cellulose.

Figure 3:
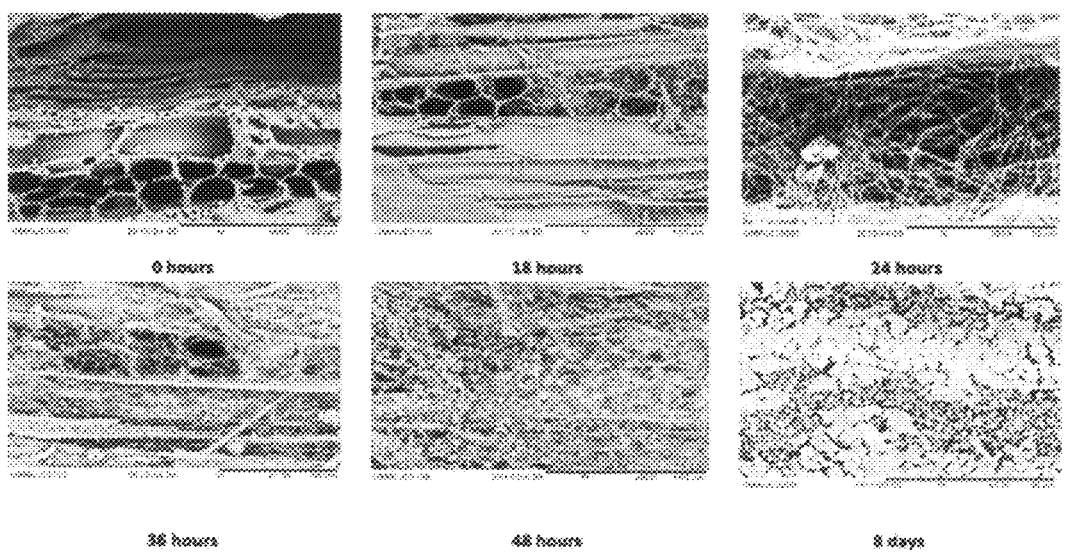
FIG. 3. shows the kinetic coverage of the cellulose adding the bacteria during the time.

Furthermore, electronic microphotographs shows how this biological system repairs and reconstitutes the damaged wood starting on the initial hours from its application to 8 days (FIG. 3). At 24 hours, a great quantity of cellulose's fibers can be shown. An efficient bio-repair process can be detected from 24 hours up to 8 days.

In USA there are 79,000,000 homes affected by termites. This biological product has a lot of advantages: is not toxic to the human, doesn't damage the environment and is a very effective as bio-repair product. It can be used as bio-repair on damaged wood's structures of homes caused by termites and other insects.

Example 2

Biological System as Insecticide

Figure 4:
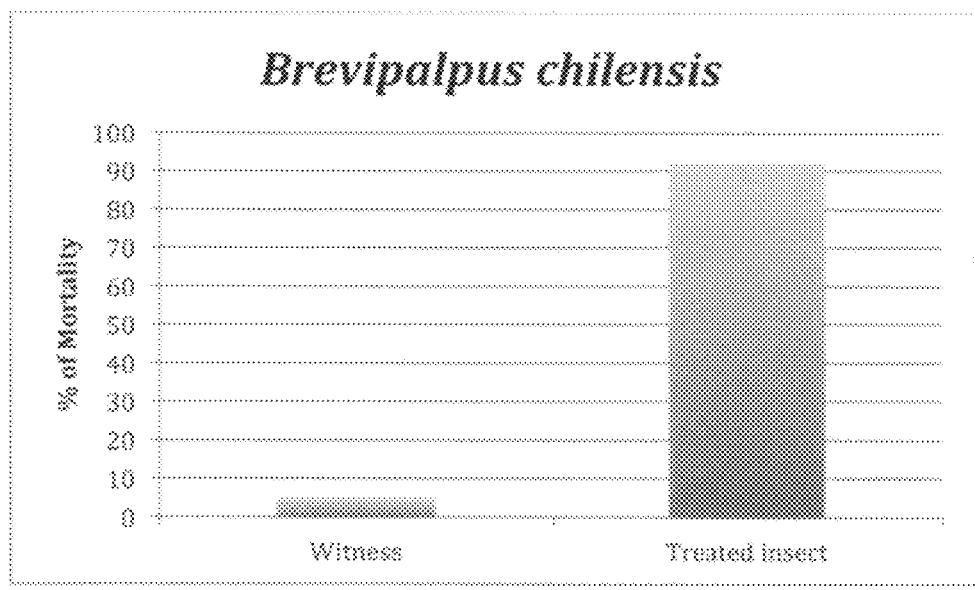
FIG. 4. shows the percentage of mortality of *Brevipalpus chilensis* with water (witness) and treated insect with culture supernatant (SN) of the bacterial cellulose culture. The SN was added to the privet leaves, not directly to the insect. After 7 days of post-treatment, the percentage of mortality was measured. This assay was performed using eggs and mobile insects. Each assay was done 10 times.

To evaluate the insecticidal effect, an aliquot of the supernatant from bacterial cellulose cultures was settled on a plate with a coleopteran to emulate the natural environmental conditions. When the coleopteran reaches the supernatant, the insect dies. Contrary to when the insect eats the bacterial cellulose. These assays were performed using Brevipalpus chilensis (a mite that infects vine plants). The SN was added to the privet leaves, not directly to the insect. After 7 days of post-treatment, we measured the percentage of mortality. A 92% of mortality was shown using the SN of the bacterial cellulose culture (FIG. 3). Also, the same assay was done, but using a 1/10 dilution of the SN (FIG. 4). We detected a 73% of mortality. So, the diluted SN is very effective.

Figure 5:
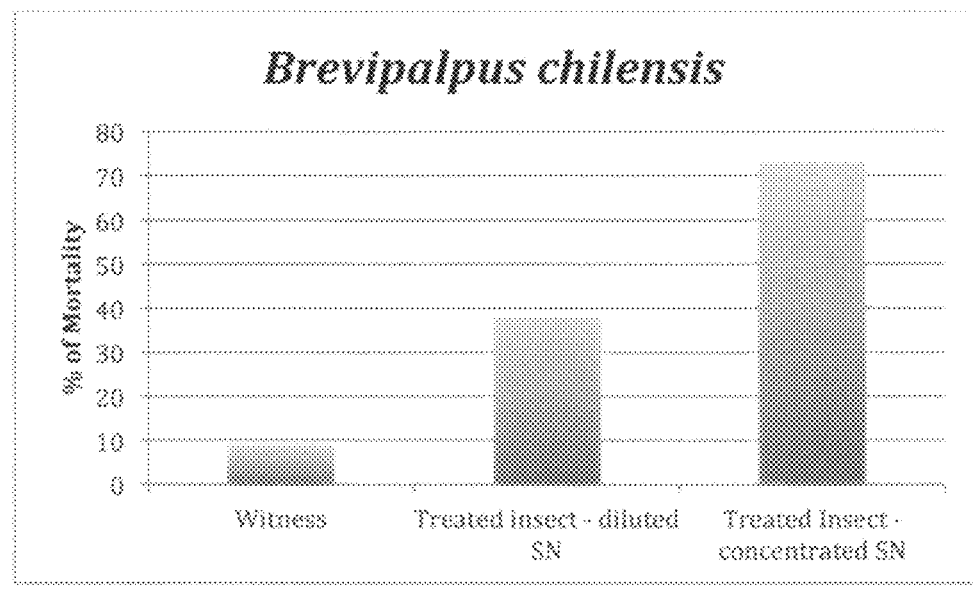
FIG. 5. Shows the percentage of mortality of *B. chilensis* using water (witness), diluted supernatant (diluted SN) and concentrated SN (direct SN of bacterial cellulose culture). The assay was done as in FIG. 3.
Figure 6:
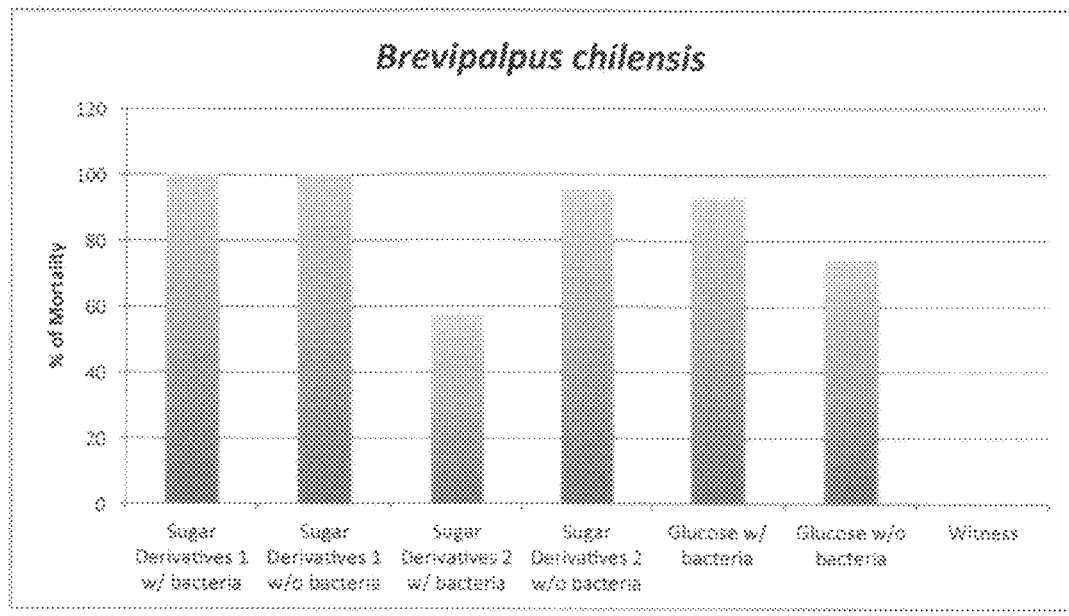
FIG. 6. shows the percentage of mortality of *B. chilensis* using supernatant (SN) of bacterial cellulose culture using different nutrient sources (sugar beet derivates 1 and 2, and glucose) with or without bacteria (treated with 0.1 N NaOH). The assay was done as in FIG. 3.

Furthermore, a similar assay was performed using SN from bacterial cellulose cultures with different nutrient source. We determined that the different SNs were effective (FIG. 5). Also, the same treatment was done with and without bacteria (SN with 0.1N NaOH). We saw activity in both treatments. We conclude that the toxin is in the bacterial cellulose supernatant.

In the vinifera vine sprouting in early may cause tissue necrosis and death cause of outbreaks and also, dehydration rachis, pedicels and bronzing of leaves.

On the other hand, we test the insecticidal effect using 9 nematodes (Table 2). Nematodes are phytoparasitic of a wide of vegetable cultivation like tomato and also vine plants. In this assay we use the SN (filtrated or not) of the liquid culture using Sugar Beet Derivate 1 as carbon source. All the insects die using the SN. Water added to the nematodes was used as negative control. The SN is effective against different types of insects.

TABLE 2

Insecticidal effect of Supernatant using Sugar Beet Molasses as nutrient sources

| Dilution | Filtrated | Not Filtrated | Water |
|---|---|---|---|
| 1 Supernatant/ 9 nematodes | 9 nematodes died | 9 nematodes died | 9 nematodes alive |
| 5 Supernatant/ 5 nematodes | 5 nematodes died | 5 nematodes died | 5 nematodes alive |

This biological product can be used as insecticide, mostly important as a termiticide to protect the wood structures from termites while this product is repairing the damaged wood as mentioned before. Also, can be used in the agriculture, mainly in the countries that are susceptible to insect damage by mites and other insects. This new biological compound shows a great potential to control the damage of Brevipalpus chilensis in our Vitis vinifera. The actually acaricides are not sufficient effective to control this mite.

Example 3

Biological System as Bio-Additive

The biological compound can be used in the fabrication of added-resistance laminated and agglomerated wood panels. Plywood increases over 5 times its resistance to flexion.

In 2011, the International Agency for Research on Cancer (IARC) classifies the formaldehyde as carcinogenic agent, based on epidemiologic studies of cancer in animals and humans. The new biological compound can replace the formaldehyde to a polymer that catalyzes the dry and reduces the use of matchwood for the Eco-wood formulation, using materials that aren't toxic on humans.

The invention claimed is:

1. A termite killing composition consisting essentially of termite killing amounts of *Gluconacetobacter malus* and *Hexaflumuron*.

* * * * *